(12) United States Patent
Hageman et al.

(10) Patent No.: US 8,759,319 B2
(45) Date of Patent: *Jun. 24, 2014

(54) LIPID COMPOSITION FOR IMPROVING BRAIN FUNCTION

(75) Inventors: Robert Johan Joseph Hageman, Wageningen (NL); Eline Marleen Van Der Beek, Wageningen (NL); Martine Groenendijk, Barendrecht (NL); Patrick Joseph Gerardus Hendrikus Kamphuis, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/620,382

(22) Filed: Sep. 14, 2012

(65) Prior Publication Data

US 2013/0018012 A1    Jan. 17, 2013

Related U.S. Application Data

(63) Continuation of application No. 12/666,619, filed as application No. PCT/NL2008/050410 on Jun. 20, 2008, now Pat. No. 8,283,335.

(30) Foreign Application Priority Data

Jun. 26, 2007   (WO) ............... PCT/NL2007/050306

(51) Int. Cl.
  *A01N 43/04*    (2006.01)
  *A61K 31/70*    (2006.01)

(52) U.S. Cl.
  USPC .................................. 514/49; 514/43; 514/50

(58) Field of Classification Search
  None
  See application file for complete search history.

(56) References Cited

U.S. PATENT DOCUMENTS

| | | | |
|---|---|---|---|
| 3,600,197 | A | 8/1971 | Spangler et al. |
| 5,378,488 | A | 1/1995 | Dimler et al. |
| 5,886,037 | A | 3/1999 | Klor et al. |
| 6,689,467 | B1 | 2/2004 | Joubert et al. |
| 6,835,750 | B1 | 12/2004 | Henderson |
| 7,090,879 | B2 | 8/2006 | Albrecht et al. |
| 8,282,965 | B2 | 10/2012 | De Kort et al. |
| 8,283,335 | B2 | 10/2012 | Hageman et al. |
| 8,361,989 | B2 | 1/2013 | Groenendijk et al. |
| 2003/0114415 | A1 | 6/2003 | Wurtman et al. |
| 2004/0001817 | A1 | 1/2004 | Giampapa |
| 2005/0208179 | A1 | 9/2005 | Albrecht et al. |
| 2006/0025376 | A1 | 2/2006 | Wurtman |
| 2006/0241077 | A1 | 10/2006 | Wurtman et al. |
| 2007/0004670 | A1 | 1/2007 | Wurtman et al. |
| 2007/0140992 | A1 | 6/2007 | Schick et al. |
| 2010/0323982 | A1 | 12/2010 | Hageman et al. |
| 2010/0331258 | A1 | 12/2010 | Kamphuis et al. |
| 2010/0331275 | A1 | 12/2010 | Groenendijk et al. |
| 2011/0006917 | A1 | 1/2011 | Taniguchi et al. |
| 2011/0009357 | A1 | 1/2011 | Hageman et al. |
| 2011/0027391 | A1 | 2/2011 | De Kort et al. |
| 2011/0105594 | A1 | 5/2011 | De Kort et al. |
| 2013/0012469 | A1 | 1/2013 | De Kort et al. |

FOREIGN PATENT DOCUMENTS

| | | |
|---|---|---|
| EP | 0 175 468 A2 | 3/1986 |
| EP | 0 891 719 A1 | 1/1999 |
| EP | 1 216 041 B1 | 2/2004 |
| EP | 1 656 839 A1 | 5/2006 |
| EP | 1 666 092 A2 | 6/2006 |
| EP | 1 800 675 A1 | 6/2007 |
| EP | 1 282 365 B1 | 12/2007 |
| JP | 64-080250 A | 3/1989 |
| JP | 6-237734 A | 8/1994 |
| JP | 10-004918 A | 1/1998 |
| JP | 10-136937 A | 5/1998 |
| JP | 11-071274 | 3/1999 |
| WO | WO-00/38829 A1 | 7/2000 |
| WO | WO-01/32034 A1 | 5/2001 |
| WO | WO-01/82928 | 11/2001 |
| WO | WO-02/088159 A1 | 11/2002 |
| WO | WO-02/096464 A1 | 12/2002 |
| WO | WO-03/013276 A1 | 2/2003 |
| WO | WO-03/041701 A2 | 5/2003 |
| WO | WO-2005/039597 A2 | 5/2005 |
| WO | WO-2006/031683 A2 | 3/2006 |
| WO | WO-2006/118665 A2 | 11/2006 |
| WO | WO-2006/127620 A2 | 11/2006 |
| WO | WO-2007/001883 A2 | 1/2007 |
| WO | WO-2007/004685 A2 | 1/2007 |
| WO | WO-2007/004689 A1 | 1/2007 |
| WO | WO-2007/008586 A2 | 1/2007 |
| WO | WO-2007/058538 A2 | 1/2007 |
| WO | WO-2007/073178 A2 | 6/2007 |
| WO | WO-2009/002145 A1 | 12/2008 |
| WO | WO-2009/002146 A1 | 12/2008 |
| WO | WO-2009/002148 A1 | 12/2008 |

(Continued)

OTHER PUBLICATIONS

U.S. Appl. No. 12/666,611, filed Dec. 23, 2009, Kamphuis, et al.

(Continued)

*Primary Examiner* — Patrick Lewis
(74) *Attorney, Agent, or Firm* — Gilberto M. Villacorta; Sunit Talapatra; Foley & Lardner LLP

(57) ABSTRACT

The invention pertains to the use of a lipid fraction for the support of brain function. The lipid fraction comprises the medium-chain fatty acids at least 4 g hexanoic acid and/or at least 5 g octanoic acid, at least 1 g eicosapentaenoic acid, and in addition more than 0.4 g α-linolenic acid per 100 g fatty acids of the lipid fraction.

21 Claims, No Drawings

(56) References Cited

FOREIGN PATENT DOCUMENTS

| WO | WO-2009/002163 A1 | 12/2008 |
| WO | WO-2009/002164 A1 | 12/2008 |
| WO | WO-2009/002165 A1 | 12/2008 |
| WO | WO-2009/002166 A1 | 12/2008 |
| WO | WO-2009/082203 A1 | 7/2009 |
| WO | WO-2009/082227 A1 | 7/2009 |

OTHER PUBLICATIONS

U.S. Appl. No. 12/666,617, filed Dec. 23, 2009, Hageman et al.
U.S. Appl. No. 12/666,621, filed Dec. 23, 2009, Groenendijk, et al.
Database WPI Week 198918, Derwent Publications Ltd., London, GB, AN 1989-134762, JP 01 080250, Mar. 27, 1989 [XP002449815].
Database WPI Week 199439, Thomson Scientific, London, GB, AN 1994-312783, JP 06 237734, Aug. 30, 1994 [XP002494932], 2 pages.
Database WPI Week 199182, Derwent Publications Ltd., London, GB, AN 1998-123754, JP 10 004918, Jan. 13, 1998 [XP002470089], 1 page.
Database WPI Week 199831, Derwent Publications Ltd., London, GB, AN 1998-355002, JP 10 136937, May 26, 1998 [XP002449814].
Database WPI Week 199921, Thomson Scientific, London, GB, AN 1999-248435, JP 11 071274, Mar. 16, 1999 [XP002495741].
Folstein et al., "'Mini-Mental State' A Practical Method for Grading the Cognitive State of Patients for the Clinician," J Psychiat Res, 1975, 12(3), pp. 189-198.
Galasko et al., "An Inventory to Assess Activities of Daily Living for Clinical Trials in Alzheimer's Disease," Alz Dis Assoc Dis, 1997, 11(Sup 2), pp. 33-39.
Hansson et al., "Association Between CSF Biomarkers and Incipient Alzheimer's Disease in Patients with Mild Cognitive Impairment: A Follow-up Study," Lancet Neurol, vol. 5, No. 3, 2006, pp. 228-234.
International Search Report, PCT/NL2007/050306, dated Sep. 26, 2007, 3 pages.
McKahnn et al., "Clinical diagnosis of Alzheimer's disease: Report of the NINCDS-ADRDA Work Group," Neurology, 1984, 34, pp. 939-944.
Pratico et al., "Increase of Brain Oxidative Stress in Mild Cognitive Impairment," Arch Neurol, vol. 59, 2002, pp. 972-976.
International Search Report corresponding to PCT/NL2008/050410, dated Sep. 19, 2008, 2 pages.
International Preliminary Report on Patentability corresponding to PCT/NL2008/050410, dated Jul. 23, 2009, 6 pages.
International Search Report for PCT/NL2008/050411 dated Nov. 5, 2008.
Katoku Y, et al. "Nutrient Compositions Containing Nucleic Acid Related Compounds, used for Growth and Health Maintenance—Contain e.g. Docosahexaenoic Acid, Arachidonic Acid and Cholesterol" WPI/THOMSON, Jan. 13, 1998 (Abstract).
Wurtman, etal. "Synaptic Proteins and Phospholipids are Increased in Gerbil Brain by Administering Uridine Plus Docosahexaenoic Acid Orally" Brain Research (2006) pp. 83-92.
International Search Report (PCT/NL2008/050406) dated Sep. 30, 2008, 3 pgs.
International Search Report for PCT/NL2008/050408 dated Aug. 8, 2008.
Notice of Allowance cited in related U.S. Appl. No. 12/666,619, dated Jun. 7, 2012.
Notice of Allowance cited in related U.S. Appl. No. 12/809,418, dated Jun. 8, 2012.
Office Action cited in related U.S. Appl. No. 12/666,617, dated Jun. 4, 2012.
Office Action cited in related U.S. Appl. No. 12/666,621, dated Jun. 4, 2012.
Quadri et al., "Homocysteine, folate, and vitamin B-12 in mild cognitive impairment, Alzheimer disease, and vascular dementia," *Am J Clin Nutr*, vol. 80, pp. 114-122 (2004).
"Derivative—Definition and More from the Free Merriam-Webster Dictionary" Retrieved Oct. 22, 2012 from http//www.merriam-webster.com/dictionary/derivative.
Albert, M. et al. "Preclinical prediction of AD using neuropsychological tests", Journal of the International Neuropsychological Society, 2001, vol. 7, pp. 631-639.
Bird, T.D., Genetic aspects of Alzheimer disease, Genetics in Medicine, Apr. 2008, vol. 10, No. 4, p. 231-237.
Cansev, M. et al. "Chronic Administration of Docosahexaenoic Acid or Eicosapentaenoic Acid, But Not Arachidonic Acid, Alone or in Combination with Uridine, Increases Brain Phosphatide and Synaptic Protein Levels in Gerbils", Neuroscience, 2007, vol. 148, pp. 421-431.
Cansev, M. et al. "Oral administration of circulating precursors for membrane phosphatides can promote the synthesis of new brain synapses", Alzheimer's & Dementia, 2008, vol. 4, pp. S153-S168.
Cole, G. et al. "Docosahexaenoic Acid Protects From Amyloid and Dendritic Pathology in an Alzheimer's Disease Mouse Model", Nutrition and Health, 2006, vol. 18, pp. 249-259.
Diagnostic and Statistical Manual of Mental Disorders (fourth Edition, 2000) 013 DSM-IV-TR; American Psychiatric Association. (table of contents only).
Freund-Levi, Y. et al. "w-3 Fatty Acid Treatment in 174 Patients With Mild to Moderate Alzheimer Disease: OmegAD Study", Arch Neurol, Oct. 2006, vol. 63, pp. 1402-1408.
Holguin, S. et al. "Chronic adminstration of DHA and UMP improves the impaired memory of environmentally impoverished rats", Behavioural Brain Research, 2008, vol. 191, pp. 11-16.
Korezyn, A. et al. "The prevention of the dementia epidemic", Journal of the Neurological Sciences, 2007, vol. 257, pp. 2-4.
Markesbery, W. et al. "Neuropathologic Substrate of Mild Cognitive Impairment", Arch Neurol, Jan. 2006, vol. 63, pp. 38-46.
Morris, J. "Mild Cognitive Impairment Is Early-Stage Alzheimer Disease", Arch Neurol., 2006, vol. 63, No. 1, 6 pgs.
Nitsch, R. et al. "Evidence for a membrane defect in Alzheimer disease brain", Proc. Natl. Acad. Sci., Mar. 1992, vol. 89, pp. 1671-1675.
Oksman, M. "Impact of different saturated fatty acid, polyunsaturated fatty acid and cholesterol containing diets on beta-amyloid accumulation in APP/PS1 transgenic mice", Neurobiology of Disease, 2006, vol. 23, pp. 563-572.
Reynolds, E. "Vitamin B12, folic acid, and the nervous system", Review, Nov. 2006, vol. 5, pp. 949-960.
Sakamoto, T. et al. "Oral supplementation with docosahexaenoic acid and uridine-5'-monophosphate increases dendritic spine density in adult gerbil hippocampus", Brain Research, 2007, vol. 1182, pp. 50-59.
Wood-Kaczmar et al. Understanding the molecular causes of Parkinson's disease, Trends in Molecular Medicine, vol. 12, No. 11 (2006), pp. 521-528.
Cormier, et al. "Diet and Child Behavior Problems: Fact or Fiction?", Pediatric Nursing, Mar.-Apr. 2007, vol. 33, No. 2, pp. 138-143.
Freemantle, et al. "Omega-3 fatty acids, energy substrates, and brain function during aging", Prostaglandins Leukotrienes and Essential Fatty Acids, 2006, vol. 75, pp. 213-220.

LIPID COMPOSITION FOR IMPROVING BRAIN FUNCTION

CROSS-REFERENCE TO RELATED APPLICATIONS

This application is a continuation of U.S. patent application Ser. No. 12/666,619, filed Apr. 2, 2010, which is a National Phase application of PCT/NL2008/050410, filed Jun. 20, 2008, and published as WO 2009/002165, which claims the benefit of priority from International Patent Application PCT/NL2007/050306, filed Jun. 26, 2007. The foregoing applications are incorporated by reference herein in their entirety.

FIELD OF THE INVENTION

The invention is related to lipid blends which comprise selected fatty acids, and the use thereof in the manufacture of nutritional or pharmaceutical products for improving brain function in a mammal, in particular in the elderly.

BACKGROUND

The nervous system, in particular the brain, plays an essential role in a mammal's life. For example cognitive, emotional, social, sensory, motoric and regulatory functions are mainly determined by the brain. In the western society more and more diseases, disorders and problems with a proper functioning of the brain are becoming recognised. Young people increasingly experience damage to the brain, for example due to intoxications such as alcohol—or drug abuse, due to traumata such as traumatic brain injury (TBI), for example as a result of sport accidents, work accidents, car accidents and the like, or systematic malnourishment. Also during aging several deleterious changes occur in the nervous system and in particular in the brain. Malfunctioning of the brain is therefore especially a problem in the elderly and more in particular in the frail or malnourished elderly. In this group, several diseases and disorders which are associated with or find their cause in a badly functioning nervous system are therefore relatively frequently observed. Examples are several forms of dementia, such as vascular dementia, Alzheimer's disease, dementia with Lewy bodies; Huntington's disease, Parkinson's disease; mood disorders, such as the various forms of depression, but also other diseases or disorders like abnormal behaviour, for example during daily living, withdrawal from social events and indecisiveness.

Many lipid blends have been used in the manufacture of foods for improving brain function. For example WO 2006/118665 discloses a method of reducing protein aggregation in the brain of a mammal by increasing endogenous ketone levels. The latter can be achieved by administering medium chain fatty acids (MCT) and a low amount of digestible carbohydrates. WO 2007/001883 discloses the use of MCT and carnitine to improve mitochondrial function. U.S. Pat. No. 6,835,750 discloses the use of MCT in a dose of 0.5-10 g/kg body weight per day to treat Alzheimer's disease. However, it is generally known that administration of high doses of MCT may result in gastrointestinal discomfort. Furthermore, MCT administration results in a satiating effect which may decrease the amount that is consumed of subsequent meals. This is often undesirable in diseased persons or the elderly. Also the ketogenic character of MCT decreases with time, which would mandate the consumption of ever increasing amounts of MCT to obtain the same ketogenic effect. Further, MCT consumption may result in increased plasma levels of for example triglycerides, which is undesirable in persons who are at risk of developing cardiovascular or cerebrovascular disorders, such as the elderly and in obese persons. EP 1282365 discloses the use of a blend which comprises omega-3 long-chain polyunsaturated fatty acids (ω-3 LCPUFA's) and phospholipids in conjunction with specific B vitamins to treat vascular diseases and dementia. JP 10136937 discloses a total nutritional food comprising docosahexanoic acid, eicosapentaenoic acid and linoleic acid for activating the function of encephalic cells.

Lipid blends have also been proposed for the treatment of disorders, other than for the support of brain function. U.S. Pat. No. 5,886,037 discloses the use of a lipid blend which comprises 55-95 wt % MCT, 5-25 wt % ω-3 LCP and 0-3 wt % other fatty acids for treatment of dyslipidaemias. EP 1216041 discloses the use of a high amount (35-70 en %) of a lipid blend with 25-70 wt % MCT and ω-6/ω-3=2-7:1 in the manufacture of a food product for the treatment of sepsis or inflammatory shock. WO 2003/013276 discloses the use of 30-70 en % of a lipid blend which is rich in oleic acid (50-70 wt %) and specific amounts of ω-6 fatty acids and 1-10 wt % ω-3 fatty acids for increasing intramyocellular lipid levels in muscle cells, which is claimed to be beneficial for endurance athletes. On the other hand, also a blend with 40-65 wt % MCT and MUFA=0-30 wt % and 20-50 wt % LC saturated fatty acids is disclosed for decreasing the accumulation of intramyocellular lipids in an individual. EP 0175468 discloses the use of a mixture of docosahexanoic acid, eicosapentaenoic acid and gamma-linolenic acid (an ω-6 fatty acid) for the treatment of cancer.

Therefore there is a need for nutritional or pharmaceutical compositions which are suitable for enteral use by a patient in need of a support of brain function, which does not have the disadvantages of prior art compositions, which demonstrates a rapid effect, and which is convenient for use and palatable.

The inventors now have found that the use of a lipid fraction, in a specific formulation of the product and optionally in combination with a protein fraction, and/or other components provides these advantages over the prior art solutions for the support of brain function, in particular in the elderly.

DESCRIPTION OF THE INVENTION

The invention is related to a lipid fraction for the support of brain function, the treatment of neurological disorders or diseases, such as Alzheimer's disease, and the decrease in cognitive function, where the lipid fraction comprises one or more sources of hexanoic acid and/or octanoic acid, a source of eicosapentaenoic acid, and more than 0.4 g α-linolenic acid per 100 g fatty acids of the lipid fraction.

The lipid fraction may be used to manufacture a nutritional or pharmaceutical product. Such product is suitable for enteral administration to a patient in need of support of his or her brain function. Preferably, the product comprises some antigens, such as proteins or peptides and the like, which make the product unsuitable for parenteral administration. Hence, the invention relates to a nutritional or pharmaceutical product comprising the lipid fraction according to the invention. The product can be used as a supplement and may have a liquid, a semi-liquid or solid form.

The liquid forms of the product as claimed can be manufactured with low viscosity, which makes them suitable for administration by tube to a patient. The viscosity of the liquid form is therefore low, preferably less than 40, more preferably 6-30 mPa·s at 20° C., measured at a shear rate of 100 sec$^{-1}$. Hence, the invention relates in particular to the use of a composition comprising the lipid fraction according to the invention, wherein the viscosity is less than 40 mPa·s, more preferably between 6 and 30 mPa·s at 20° C., measured at a shear rate of 100 sec$^{-1}$.

Preferably, the liquid product comprises a protein fraction, a lipid fraction and a carbohydrate fraction, as well as vitamins and minerals or trace elements in order to provide full support of brain function in patients with varying nutritional status. It is important that despite the inclusion of all these ingredients, the osmotic value remains below 500, more preferably 200-470 mOsm per kg product in the product, in order to increase compliance and increase brain support in especially elderly patients. Gastrointestinal discomfort is prevented by this measure. These osmolality values are also applicable in products having a pH between 3.8 and 7 and which are flavoured. The latter properties are important for obtaining superior palatability of the product and an excellent compliance with recommended administration protocols in the longer term. Hence, the invention relates in particular to the use of a composition comprising the lipid fraction according to the invention, wherein the osmotic value is less than 500 mOsm, more preferably between 200 and 470 mOsm per kg product.

The ready to consume products which have a lipid level above 45 en %, preferably more than 55 en %, most preferably more than 60 en %, up to e.g. 75 en %, will preferably have a higher dry mass content per unit dose than conventional products. Good compliance with prescription protocols can be obtained when such products have a dry mass content of more than 32 g per 100 g, preferably 35-96 g per 100 g, more preferably 40-95 g per 100 g, especially 45-80 g per 100 g ready to use product. Examples are ice cream, puddings and bars, which are known in the art.

The products, in particular liquid products will have an energy density of more than 0.9 kcal/ml, preferably 1-7 kcal/ml (4.2-29.4 kJ/ml), and most preferably 2.4-6.5 kcal/ml (10.1-27.3 kJ/ml). Hence, the invention further relates to the use of a composition comprising the lipid fraction according to the invention, having an energy density of more than 0.9 kcal/ml, preferably 1-7 kcal/ml (4.2-29.4 kJ/ml), and most preferably 2.4-6.5 kcal/ml (10.1-27.3 kJ/ml).

The lipid fraction as described below in detail has been developed to fully support brain function. Nutritional status of neuronal cells, in particular of neurons, astrocytes and glial cells is improved against prior art lipid blends. Such status can for example be monitored by measuring atrophy of the brain cells, for example by applying MRI (magnetic resonance imaging) methods as known in the art, or determining biochemical or physiological properties of the brain, e.g. by applying PET (positron emission tomography), analysis of cerebrospinal fluid composition or single photon emission tomography (SPECT).

The lipid fraction comprises at least 0.4, preferably 1-12 weight percent (wt %) α-linolenic acid (aLA), and preferably at least 0.4, preferably 1-20 wt % eicosapentaenoic acid (EPA) based on the sum of fatty acids in that fraction. Suitable sources for increasing the amount of aLA include canola oil and flax seed oil.

The lipid fraction preferably comprises docosahexaenoic acid (DHA) in an amount of at least 0.5, preferably 1-35, more preferably 5-30 wt % of the sum of fatty acids in that fraction and wherein the weight ratio of DHA to EPA is preferably in the range 0.2-7, more preferably 0.8-4. The inclusion of these amounts of DHA in the lipid blend will improve nutritional status of brain cells.

The lipid fraction comprises preferably more than 15 g DHA, preferably more than 3 g EPA and preferably more than 1 g linolenic acid and preferably more than 3 g, preferably 4-20 g hexanoic acid and preferably more than 4 g, preferably 5-20 g octanoic acid, per 100 g of all fatty acids. The inclusion of all these fatty acids in these amounts not only improve nutritional status but also may influence the other properties of the brain cells in such a way that a net support of the brain function can be observed.

The weight amount of α-linolenic acid is preferably 0.3-1 times the weight amount of linoleic acid in the lipid fraction. It is thought by the inventors that the relatively high amount of α-linolenic acid compared to linoleic acid is not due to a direct effect on the brain cells but instead works indirectly, despite the early nature of the effect that is observed.

The lipid fraction preferably comprises 10-60, more preferably 25-45, most preferably 28-40 g medium chain triglycerides (MCT) per 100 g of the lipid fraction in the product (or the same amounts of the medium-chain fatty acids on 100 g of all fatty acids). Following the dosing regimens for the product, this results in a dose of less than 0.5 g MCT per kg bodyweight per day in order to prevent gastrointestinal discomfort.

The medium-chain fatty acids (MCT) are defined to be linear or branched saturated carboxylic acids having six, seven, eight, nine or ten carbon atoms. Best results in terms of support of brain function are obtained with linear fatty acids having 6, 7 or 8 carbon atoms and the weight amount of the sum of these fatty acids compared to the sum of the weight amount of 9 and 10 carbon atoms should preferably be more than 2.5.

The best sources of medium chain fatty acids are MCT or selected fractions rich in medium chain fatty acids from coconut oil, lipids or butter from milk, palm kernel oil or palm oil. The sources provide triglycerides with a high content of hexanoic (C6:0) and octanoic acid (C8:0) and may also comprise C10:0 or other fatty acids. It is important that the doses of C6:0 and C8:0 are met, as are the other requirements for the lipid blend. This may result in the use of sources of MCT which have a low level of C10:0. In particular such MCT comprise less than 20 wt % C10:0, preferably less than 15 wt % of the fatty acid in that MCT oil. The total amount of C10 fatty acids is preferably less than 10 wt. % of all fatty acids of the composition, more preferably less than 7 wt. %

Also, good results can be obtained when at least one source of hexanoic acid and/or octanoic acid is used which provides 45-100 wt % of hexanoic acid and/or octanoic acid based on the total amount of fatty acids in that source and wherein that source is not medium chain triglyceride oil (MCT). Such sources include di- or monoglycerides comprising one or two saturated fatty acids having a carbon number of 6-10. The use of such ingredients increases palatability and decreases gastrointestinal discomfort alter consumption of doses of a bolus of 40 g lipids. Hence, the invention also relates to the use of a lipid fraction comprising a source of di- and monoglycerides, said source providing 45-100 wt % of hexanoic acid and/or octanoic acid, based on the total amount of fatty acids, for improving brain function, The lipid fraction comprises preferably at least 6 wt % of phospholipids or lysophospholipids. This decreases the risk of gastrointestinal discomfort of a product rich in triglycerides comprising hexanoic and octanoic acids. It also facilitates bioavailability of the trace elements and vitamins.

The lipid fraction preferably contributes more than 45%, more preferably 48-70% of the energy of the product after administration to a human, using the Atwater factors for digestible carbohydrates (4 kcal/g), proteins (4 kcal/g) and lipids (9 kcal/g) and zero for the organic acids and nutritional fiber, minerals and vitamins in the product. Despite the fact that these products comprise a relatively high amount of lipids, and in particular MCT, administration thereof does not lead to the negative side effects as frequently observed by prior art high fat products. These side effects include strong satiating, gastrointestinal discomfort such as sickness and diarrhea, but also include impartment of the availability of other components in the product such as vitamins, trace elements and decreased digestion rates of proteins and carbohydrates. These advantages are thought to be attributed to the selection of the lipid blend alone and in combination with the selection of the nature of the other components of the product.

The lipid fraction comprises preferably more than 10 wt % MCT and preferably 0.1-40 wt %, more preferably 1-32 wt %, especially 2-20 wt % of ω-3 LCP (ω-3 LCP being defined as ω-3 fatty acids having at least two unsaturated carbon-carbon bonds and at least 20 carbon atoms).

The amount of free fatty acids is preferably less than 2 wt %, more preferably less than 1 wt % in the lipid blend in order to minimise gastrointestinal discomfort.

The lipid fraction is defined to be the part of the ready to use product which is obtained by extraction of that product with a suitable solvent using the accepted method for that particular product as published in the AOAC (American Organisation of Analytical Chemists) Handbook published in 1995. The lipid fraction thus also comprises phospholipids, glycolipids, ceramides, mono-, di- and triglycerides etc.

Preferably the lipid fraction is used in combination with a nucleotide fraction in the product for the support of brain function. Best results in efficacy and low undesired side effects are obtained when the nucleotide fraction comprises a uridine or cytidine source.

The uridine source is preferably selected from the group of uracil, uridine, phosphate forms of uridine like uridine monophosphate, diphosphate, or triphosphate, their salts and the esters of uridine or is phosphates with carboxylic acids in monomeric or in polymeric form. In particular those derivatives of uridine are effective, wherein the uridine has been acylated with acetic acid, n-caproic acid, caprylic acid, or n-capric acid, because these increase the bioavailability of the uridine source. Methods for reacting these medium chain fatty acids to uridines, for example to the 5' position of the uridine are known in the art per se for other fatty acids and comprise conventional acylation methods.

The invention also relates to compositions containing 0.05-100 wt. %, especially 0.2-10 wt. % of these uridine C6-C10 acylates, the remainder being food or food-grade component, which especially may comprise 1-75 wt. % of a lipid fraction. The invention also relates to a mixture of the uridine C6-C10 acylates with a lipid composition in a weight ratio between 1:200 and 1:1, especially between 1:60 and 1:3.

Doses that must be administered are given as UMP. The amount of other uracil sources can be calculated by taking the molar equivalent to the UMP amount Similarly the cytidine source is preferably selected from the group of cytidine, its phosphates, its salts and esters of cytidine. Also similar as for uracil doses between various cytidine forms can be compared and calculated into each other.

In order to obtain a better improvement of brain function the sum of the weight amount of uridine, calculated to uracil equivalents, cytidine, calculated to cytosine is at least 2 times, preferably at least 4 times the weight amount of adenine, guanine, thymine, inosine or other nucleobases.

Best efficacy is obtained and least undesired side effects are obtained when the doses UMP or CMP is per 100 ml ready to use product at least 40 mg, preferably 50-6000, more preferably 60-1000 mg. Most preferably 70-600 mg UMP is included per 100 g of ready to use product. The amount top be used per 100 g pf lipid fraction is preferably at 100 mg, more preferably 200 mg-20 g, most preferably 400 mg-10 g per 100 g lipid.

Preferably the product comprises a fibre fraction which comprises food grade nutritional fibres. More preferably the fibre comprises more than 10 wt %, especially more than 20 wt. % oligomeric indigestible material having a chain length of 3 to 20 saccharide units. In particular, when the fibre blend comprises (e.g. at least 10 wt. %) oligosaccharides of arabans, mannans, uronic acids (e.g. galacturonans) or galactans or mixtures thereof, such benefits are observed. In a particular embodiment the fibres comprise at least 20 wt %, especially at least 30 wt. % of oligo- and polysaccharides having a molecular weight in the range of 500-10.800 (=DP 3-60). Even better results are obtained when the fibre fraction comprises a mixture of oligosaccharides (3-20 units), and polymeric fibres which have a chain length of more than 60 saccharide units, and possibly polymeric fibres of intermediate length (20-60 units). The polymeric fibres include cellulose and hemicellulose-type fibers, like those in pea and soy.

Suitable oligo saccharides are synthetic oligosaccharides like galacto-oligosaccharides, or hydrolysed natural fibres, like hydrolysed guar or hydrolysed beet fibre or hydrolysed pectin or mixtures thereof. In order to obtain best results, the weight amount of fibre in the product should be 0.04-2, preferably 0.07-1, more preferably 0.1-0.8 times the weight amount of lipids in the product. Gastrointestinal discomfort and postprandial lipid profile is significantly improved when the fibre blend is included in the MCT enriched formula.

Other components that beneficially are included are carnitine, vitamins, trace elements, minerals as known in the art. It is preferred to include at least one of folic acid, vitamin B12 and vitamin B6 in the product and more preferably all three. Folic acid should be included per 100 ml ready to use product in an amount of 50-500 µg, vitamin B6 in an amount of 0.5-5 mg and vitamin B12 0.8-100 µg, or the same amount in a daily dosage unit. With respect to the lipid fraction, the amounts are preferably 0.5-10 mg folic acid, and/or 5-100 mg vitamin B6, and/or 8-2000 µg vitamin B12 per 100 g lipid.

Suitable carnitine sources include L-carnitine or the acyl carnitines known in the art, such as acetyl, butyryl, isobutyryl or propionyl carnitine. Suitable doses are 2-100, preferably 10-80 mg per 100 ml ready to use product or per daily dosage unit.

The product may further comprise proteinaceous material and digestible carbohydrates. The amount of digestible carbohydrates preferably is less than 50%, more preferably 5-45%, most preferably 10-40% of the total energy content.

The product can be used in an amount of 50-400 ml, especially 75-200 ml, most preferably 100-150 ml per day, based on the ready-to-use liquid. The amount of lipid fraction to be used per day may range from 1 to 100 g, especially 2.5-50 g, most preferably 4-20 g of lipid fraction per day or per daily dosage unit.

The product is useful in the improvement or support of brain function, in humans in need of support of brain function, which can be of any age, such as infants, children, adolescents, young adults, adults and elderly. Especially envisioned is the support of brain function in humans at risk for or suffering from injury of the central nervous system, e.g. brain trauma or spinal cord injury, such as resulting from car accidents, sports accidents, work accidents, combat situations, and the like. In particular is envisioned the elderly, more in particular the frail elderly or non-obese elderly. The product can be effective in humans who are apoE4 positive or negative.

The product has the further advantages of decreasing the plasma levels of triglycerides and dicarboxylic acids after consumption of the product compared to the consumption of prior art products that comprise conventional lipid blends. Also the urinary excretion of dicarboxylic acids like adipic acid, suberic and sebacic acid decrease, which is more physiological and support a better use of ketone bodies by the consumer. No side effects are observed such as gastrointestinal discomfort, or a negative influence on brain size or brain growth. The products are highly palatable and appear to create better availability of minerals and vitamins compared to prior art preparations having a similar lipid concentration in the product. These advantages are due to one or more of the differences with prior art formulations.

The inclusion of the hexanoic (C6:0) and/or octanoic acid (C8:0) allows the inclusion of lower amounts of DHA to have the same effect as higher doses of DHA in a product with a lipid blend which does not comprise hexanoic acid and/or octanoic acid. The inclusion of the medium-chain fatty acids in a lipid blend with DHA also allows the inclusion of lower amounts of medium-chain triglycerides fatty acids while observing the same efficacy as higher doses of medium-chain triglycerides without the lipids blend with DHA.

Support of brain function is meant to be an improvement of skills is related to activities of daily living, cognition, social skills, decision making skills, motoric skills and abilities to live independently from the help of others. Such improvement can be measured by determination of the abilities of the persons to practice them. Activities of daily living include instrumental activities, operational activities, and basal activities. These activities include the ability to use household appliances, to coordinate one's movements, to make rapid movements, to walk, do the laundry, do the dishes, to apply hygienic practices, to travel, etcetera.

The brain function is also supported in a prodromal patient for a neurological disorder, in a patient suffering from a cognitive decline or in a patient suffering from senile dementia, Alzheimer's disease, diabetes or insulin resistance or in a patient who experienced a physical trauma or toxicological trauma.

The product according the invention demonstrates rapid efficacy. If prior art formulations would demonstrate efficacy, they demonstrate this after at least weeks of use. The current formulations demonstrate an efficacy within hours or days after the start of using the formulation.

Standardised protocols are known in the art to measure in a scientifically sound and reliable way the measure of skills as mentioned above.

EXAMPLES

Example 1

Liquid for Use in a Prodromal Patient

The liquid comprises per 100 ml 3 g protein (as casein/whey 80/20), 7 g lipid (MCT/canola/phospholipids/marine oils in a weight ratio of 50/30/6/14) and 8 g digestible carbohydrates (as maltodextrin 19/fructose/lactose in a ratio 60/10/30) and further:
  UMP 500 mg [other nucleotides<10 mg]; cholin 300 mg;
  Vitamin B6 1.1 mg; vit B12 2.3 µg; folic acid 300 µg; Other trace elements, minerals and vitamins according to the art for supplements;
  Galactooligosaccharides 0.6 g; pea fiber 0.6 g
  Giving an osmolality of 490 mOsm/kg water The drink is to be administered in an amount of 125 ml per day during one week to a prodromal dementia patient in order to see the effect on brain function and in particular better social skills, more activities and fitness and better cognitive function, and a better alertness and ability to concentrate and pay attention.

Example 2

Bar for use in a patient suffering from Alzheimer's Disease once or twice per day.
The bar comprises per 25 g dry mass:
  10.5 g Lipids: (40 MCT; milk fat 25, fish oil 15, canola 15, chocolate 5)
  3 g protein (milkprotein)
  9 g carbohydrates (glucose syrup)
  1 g premix providing 100 ug folic acid, 2 ug vitamin B12 and 1 mg vitamin B6 and 200 mg UMP
  1.5 g fiber (GOS 10, hydrolyzed guar 40, soy fiber 50)

Example 3

Liquid for use in a person suffering from cognitive decline.
At least 200 ml per day should be consumed by the person of the product which comprises per 100 ml:
  Energy 600 kcal
  Protein 3.1 g milk protein
  Lipids 14.6 g; 7 g C6:0+C8:0; 0.2 g α-linolenic acid; 0.6 g eicosapentaenoic acid and 0.9 g docosahexaenoic acid, 5.9 g other fatty acids
  Carbohydrates 0.6 g
  UMP 500 mg
  Fiber: 1.5 g of a 1:1 mixture of beet fiber and hydrolysed pectin
  Vitamin A 253 IU; vitamin D 2.2 IU; vitamin C 9 mg; vitamin K 6 µg; thiamin 0.14 mg; riboflavin 0.15 mg; niacin 1.5 mg; vitamin B6 1.1 mg; folic acid 100 µg; vitamin B12 0.9 µg, biotin 4 µg; pantothenic acid 0.6 mg; inositol 4 mg; Na 4.3 mg; K 4.1 mg; Cl 4.3 mg; Ca 86 mg; P 100 mg; Mg 22 mg; Zn 1.2 mg; Fe 1.5 mg; Cu 0.12 mg; Mn 0.13 mg; Iodide 18 µg; Mo 6 µg; Se 4.4 µg; Cr 3 µg Example 4

Liquid drink for support of brain function in the elderly, which comprises per 100 ml:
  Energy 630 kJ.
  Protein 6.0 g casein
  Lipids 8.7 g comprising a mixture of 50 wt % MCT oil, 15% marine oil and 35 wt % vegetable oils
  Carbohydrates 12 g (80 maltodextrins, 20 glucose syrup)
  Dietary fiber 1.2 g of blend of example 3
  UMP 400 mg
  Other trace elements, minerals and vitamins according the art for supplements Example 5

Bar suitable for use in a person suffering from physical brain trauma comprising per 50 g:
  12 g lipid fraction (7.2 g diglycerides having per 100 g fatty acids therein 80 g of the sum of hexaenoic acid and octanoic acid, 2.4 g flaxseed oil, 1.2 g marine oil, 1.2 g soy lecithin),
  21 g digestible carbohydrates (maltodextrins, glycerol)
  11 g skimmed milk powder
  1.3 g ash
  4.7 g water

The invention claimed is:

1. A method of supporting brain function, comprising administering to a person in need thereof a composition comprising a lipid fraction comprising hexanoic acid and/or octanoic acid; eicosapentaenoic acid (EPA); and more than 0.4 g alpha-linolenic acid per 100 g fatty acids of the lipid fraction.

2. The method according to claim 1, wherein the lipid fraction comprises:
   (a) docosahexaenoic acid (DHA) in an amount of at least 10 wt % of the sum of fatty acids in the lipid fraction and wherein the weight ratio of DHA to EPA is 0.2-7; and/or
   (b) 10-60 g medium chain triglycerides (MCT) per 100 g of the lipid fraction; and/or
   (c) linoleic acid and wherein the weight amount of alpha-linolenic acid is 0.3-1 times the weight amount of linoleic acid in the lipid fraction; and/or
   (d) 10-60 wt % MCT and 1-30 wt % omega-3 LCP; and/or
   (e) at least 6 wt % of phospholipids or lysophospholipids.

3. The method according to claim 1, wherein the lipid fraction comprises, per 100 g fatty acids, more than 15 g DHA, more than 3 g EPA, more than 1 g alpha-linolenic acid, more than 4 g hexanoic acid and more than 5 g octanoic acid.

4. The method according to claim 1, wherein at least one source of hexanoic acid and/or octanoic acid is used which provides 45-100 wt % of these fatty acids based on the total amount of fatty acids in that source and wherein that source is not medium chain triglyceride oil.

5. The method according to claim 1, wherein the lipid fraction contributes 45-70% of the energy of the product after administration to a human.

6. The method according to claim 1, wherein the lipid fraction is combined with of a nucleotide fraction, and wherein the nucleotide fraction comprises a uridine or a cytidine source.

7. The method according to claim 6, wherein the uridine source is selected from the group of uracil, uridine, phosphate forms of uridine, esters of uridine with carboxylic acids, and the cytidine source is selected from the group of cytidine, its phosphates, esters of cytidine and wherein the sum of the weight amount of uridine, calculated to uracil equivalents, cytidine, calculated to cytosine is at least 2 times the weight amount of adenine, guanine, thymine, inosine or other nucleobases.

8. The method according to claim 6, wherein the uridine source is UMP, and is present in an amount of 200 mg-20 g per 100 g lipid.

9. The method according to claim 1, wherein the lipid fraction is combined with a fiber fraction comprising an oligosaccharide.

10. The method according to claim 9, wherein the fiber fraction comprises more than 10 wt %, oligomeric indigestible material having a chain length of 3 to 20 saccharide units.

11. The method according to claim 9, wherein the fiber fraction comprises a mixture of oligosaccharides of 3-20 units, and polymeric fibers of more than 60 saccharide units, and, optionally, polymeric fibers of intermediate length of 20-60 units.

12. The method according to claim 9, wherein the oligosaccharides are synthetic oligosaccharides, or are hydrolysed natural fibers.

13. The method according to claim 12, wherein the hydrolysed natural fibers comprise hydrolysed guar, hydrolysed beet fiber, hydrolysed pectin or mixtures thereof.

14. The method according to claim 1, wherein the support of brain function is related to activities of daily living, cognition, social skills, decision making skills, motoric skills and abilities to live independently from the help of others.

15. The method according to claim 1, wherein the brain function is supported in a prodromal patient for a neurological disorder, or in a patient suffering from senile dementia, from Alzheimer's disease, from diabetes or insulin resistance or from a physical trauma or toxicological trauma.

16. A product comprising a lipid fraction comprising hexanoic acid and/or octanoic acid, eicosapentaenoic acid, and more than 0.4 g alpha-linolenic acid per 100 g fatty acids of the lipid fraction.

17. The product according to claim 16, wherein the weight amount of fibre in the product is 0.04-2 times the weight amount of lipids in the product.

18. The product according to claim 16, having a dry mass content of more than 32 g per 100 g ready to consume product.

19. A method of supporting brain function, comprising administering to a person in need thereof a product according to claim 16.

20. The method according to claim 19, wherein the support of brain function is related to activities of daily living, cognition, social skills, decision making skills, motoric skills and abilities to live independently from the help of others.

21. The method according to claim 19, wherein the brain function is supported in a prodromal patient for a neurological disorder, or in a patient suffering from senile dementia, from Alzheimer's disease, from diabetes or insulin resistance or from a physical trauma or toxicological trauma.

* * * * *